United States Patent
Kim et al.

(10) Patent No.: US 10,723,863 B2
(45) Date of Patent: *Jul. 28, 2020

(54) PLASTICIZER COMPOSITION, RESIN COMPOSITION AND METHODS OF PREPARING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 75 days.

This patent is subject to a terminal disclaimer.

(21) Appl. No.: 15/767,093

(22) PCT Filed: Jun. 13, 2017

(86) PCT No.: PCT/KR2017/006145
§ 371 (c)(1),
(2) Date: Apr. 9, 2018

(87) PCT Pub. No.: WO2017/217739
PCT Pub. Date: Dec. 21, 2017

(65) Prior Publication Data
US 2018/0298162 A1    Oct. 18, 2018

(30) Foreign Application Priority Data

Jun. 15, 2016 (KR) .......... 10-2016-0074499
Jun. 9, 2017  (KR) .......... 10-2017-0072508

(51) Int. Cl.
| C08K 5/1515 | (2006.01) |
| C07D 303/42 | (2006.01) |
| C08F 14/06  | (2006.01) |
| C08K 5/101  | (2006.01) |
| C08K 5/00   | (2006.01) |

(52) U.S. Cl.
CPC .......... C08K 5/1515 (2013.01); C07D 303/42 (2013.01); C08F 14/06 (2013.01); C08K 5/0016 (2013.01); C08K 5/101 (2013.01); C08K 2201/014 (2013.01)

(58) Field of Classification Search
CPC .... C08K 5/1515; C08K 5/0016; C08K 5/101; C08K 2201/014; C07D 303/42; C08F 14/06; C08L 27/06
USPC ........................................... 524/114
See application file for complete search history.

(56) References Cited

U.S. PATENT DOCUMENTS

| 9,321,901 B2 | 4/2016 | Frenkel et al. |
| 9,593,091 B2 | 3/2017 | Kaujalgikar et al. |
| 2012/0181058 A1 | 7/2012 | Chaudhary et al. |
| 2014/0309345 A1 | 10/2014 | Frenkel et al. |
| 2014/0323622 A1 | 10/2014 | Chaudhary et al. |
| 2015/0240050 A1* | 8/2015 | Rao ................. C08K 5/0016 428/35.2 |
| 2015/0252014 A1 | 9/2015 | Kaujalgikar et al. |
| 2015/0337112 A1 | 11/2015 | Ghosh-Dastidar et al. |
| 2015/0368431 A1 | 12/2015 | Ghosh-Dastidar et al. |
| 2016/0060426 A1 | 3/2016 | Woldt et al. |
| 2018/0072867 A1 | 3/2018 | Kim et al. |

FOREIGN PATENT DOCUMENTS

| CN | 103975011 A | 8/2014 |
| CN | 104781328 A | 7/2015 |
| CN | 105008447 A | 10/2015 |
| CN | 105384963 A | 3/2016 |
| EP | 3327074 A1  | 5/2018 |
| JP | 2003072289 A | 3/2003 |
| JP | 5757952 B   | 8/2015 |
| JP | 5841946 B   | 1/2016 |
| KR | 1020140116371 A | 10/2014 |
| KR | 1020150087213 A | 7/2015 |
| KR | 1020150087214 A | 7/2015 |
| KR | 101570386 B | 11/2015 |
| KR | 1020150131016 A | 11/2015 |

OTHER PUBLICATIONS

Greenspan, et al: "Epoxy Fatty Acid Ester Plasticizers", XP055046762, Industrial and Engineering Chemistry, Dec. 1, 1953, pp. 2722-2726.

* cited by examiner

*Primary Examiner* — Josephine L Chang
(74) *Attorney, Agent, or Firm* — Dentons US LLP

(57) ABSTRACT

The present disclosure relates to an environmentally friendly plasticizer composition suitable for use in applications such as a resin for a food wrapping material, comprising an epoxidized alkyl ester composition including one or more compounds represented by the following Chemical Formula 1 and having an iodine value (I.V.) of less than 3.5 g $I_2$/100 g, and a resin composition including the same, and methods of preparing the same:

[Chemical Formula 1]

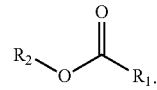

10 Claims, No Drawings

PLASTICIZER COMPOSITION, RESIN COMPOSITION AND METHODS OF PREPARING THE SAME

CROSS-REFERENCE TO RELATED APPLICATION

This application is a National Stage Application of International Application No. PCT/KR2017/006145, filed Jun. 13, 2017, and claims the benefit of Korean Patent Application No. 10-2016-0074499, filed Jun. 15, 2016, and Korean Patent Application No. 10-2017-0072508, filed on Jun. 9, 2017, contents of which are incorporated herein by reference in their entirety for all purposes as if fully set forth below.

TECHNICAL FIELD

The present invention relates to a plasticizer composition, a resin composition and methods of preparing the same.

BACKGROUND ART

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, trimellitate-, and other polymer-based plasticizers.

Generally, a plasticizer is used as a material for various products such as electric wires, pipes, flooring materials, wallpaper, sheets, artificial leather, tarpaulins, tape and food wrapping materials obtained in the related industries according to a processing method such as extrusion molding, injection molding or calendering after suitably adding various additives including resins such as polyvinyl chloride (PVC), fillers, stabilizers, pigments, and anti-fog agents to provide various processing properties.

In the current plasticizer market, environmentally-friendly plasticizers are competitively developing in the related field due to environmental issues of phthalate plasticizers, and recently, new products for overcoming the inferiority of di(2-ethylhexyl)terephthalate (DEHTP) in qualities such as plasticization efficiency, migration ability and the like, which are being used as general purpose products among such environmentally-friendly plasticizers, have been developed.

Therefore, it is necessary to continue conducting research on technology for developing products with a new composition, which has properties superior to those of DEHTP or includes DEHTP, to be optimally applied as a plasticizer for a vinyl chloride-based resin.

Meanwhile, a wrap film for a food wrapping material requires transparency for observing food with the naked eye and an elongation rate, tensile strength, an annealing property, volatile loss and adhesiveness for easily wrapping food. As a plasticizer currently used in the market of a wrap film for a food wrapping material, terephthalate-, chemical material-substituted glyceride- and glycol-based plasticizers have been used, and they are products for replacing existing adipate-based products such as dioctyl adipate. Also, there will be a continuous demand for environmentally friendly products, and it is necessary to conduct research on the development of plasticizers which are environmentally friendly and have satisfactory quality.

DISCLOSURE

Technical Problem

Therefore, during research on plasticizers, the present inventors developed a plasticizer composition, which is an environmentally friendly material that can improve inferior properties caused by structural restraints, can bring about a balanced synergistic effect on all properties such as an elongation rate, tensile strength, plasticization efficiency, migration loss and volatile loss compared to an existing plasticizer by controlling the number of carbon atoms of an alkyl moiety and the iodine value and oxirane content of an epoxidized alkyl ester composition, can also exhibit improved adhesiveness, transparency and color when used for a wrap film such as a food wrapping material, and simultaneously can maintain or improve mechanical properties such as tensile strength, an elongation rate, and thus completed the present invention.

That is, the present invention is directed to providing a plasticizer, which may improve properties such as plasticization efficiency, migration ability, tensile strength, an elongation rate, volatile loss, an annealing property and adhesiveness, which are required for treatment of sheets and films when used as a plasticizer of a resin composition, a method of preparing the same and a resin composition including the same.

Technical Solution

In one aspect, the present invention provides a plasticizer composition which includes an epoxidized alkyl ester (epoxidized fatty acid alkyl ester (eFAAE)) composition including one or more compounds represented by the following Chemical Formula 1 and having an iodine value (I.V.) of less than 3.5 g $I_2$/100 g.

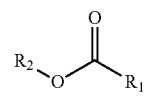

[Chemical Formula 1]

In Chemical Formula 1, $R_1$ is an alkyl group having 8 to 20 carbon atoms and including one or more epoxy groups, and $R_2$ is an alkyl group having 4 to 10 carbon atoms.

The epoxidized alkyl ester composition may include an epoxy alkyl ester composition including one or more compounds represented by Chemical Formula 1, and may further include an alkyl ester composition including one or more compounds represented by the following Chemical Formula 2.

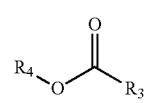

[Chemical Formula 2]

In Chemical Formula 2, $R_3$ is an alkyl group having 8 to 20 carbon atoms, and $R_4$ is an alkyl group having 4 to 10 carbon atoms.

In Chemical Formula 1, $R_2$ may be selected from the group consisting of a butyl group, an isobutyl group, a pentyl group, a hexyl group, a heptyl group, an isoheptyl group, an octyl group, a 2-ethylhexyl group, a nonyl group, an isononyl group, a 6-methyloctyl group, a decyl group, an isodecyl group and a 2-propylheptyl group.

The epoxidized alkyl ester composition may include two or more compounds having a different number of carbon atoms in $R_2$ of Chemical Formula 1.

The epoxidized alkyl ester composition may have an oxirane content (O.C.) of 3.5% or more.

The epoxidized alkyl ester composition may have an oxirane index (O.I.) of 1.0 or more.

In another aspect, the present invention provides a resin composition which includes 100 parts by weight of a resin; and 5 to 150 parts by weight of the plasticizer composition according to claim 1.

The resin may be one or more selected from the group consisting of ethylene vinyl acetate, polyethylene, polyketone, polypropylene, polyvinyl chloride, polystyrene, polyurethane and a thermoplastic elastomer.

Advantageous Effects

A plasticizer composition according to an embodiment of the present invention can ensure an environmentally-friendly property and can bring about a balanced synergistic effect on all properties such as an elongation rate, tensile strength, plasticization efficiency, migration loss and volatile loss when used in a resin composition. Also, the plasticizer composition can improve adhesiveness, transparency and color, and simultaneously can maintain or improve mechanical properties such as tensile strength, an elongation rate when used in a wrap film such as a food wrapping material.

Modes of the Invention

Hereinafter, the present invention will be described in detail.

The term "epoxidized alkyl ester" used herein refers to a material in which an alkyl group of a fatty acid ester contains an epoxy group, which is prepared from a glyceride-based compound (monoglyceride, diglyceride or triglyceride) such as natural oils through epoxidation and optionally through trans-esterification. An epoxidized alkyl ester is commonly called an epoxidized fatty acid alkyl ester (eFAAE) in the art, but "fatty acid" may be omitted, and "alkyl" may refer to an alkyl group that is bound to oxygen of an ester group.

For example, an epoxidized alkyl ester which is esterified by methanol may be epoxidized fatty acid methyl ester (eFAME), and an epoxidized alkyl ester which is esterified by 2-ethylhexanol may be epoxidized fatty acid 2-ethylhexyl ester (eFAEHE or eFAOE).

Plasticizer Composition

According to an embodiment of the present invention, there is provided a plasticizer composition which includes an epoxidized alkyl ester composition including one or more compounds represented by the following Chemical Formula 1 and having an iodine value (I.V.) of less than 4 g $I_2$/100 g.

[Chemical Formula 1]

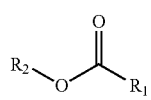

In Chemical Formula 1, $R_1$ is an alkyl group having 8 to 20 carbon atoms, which includes one or more epoxy groups, and $R_2$ is an alkyl group having 4 to 10 carbon atoms.

The epoxidized alkyl ester composition may include one or more epoxidized fatty acid alkyl esters (eFAAE), specifically, one or more compounds represented by Chemical Formula 1, and "alkyl" of the epoxidized alkyl ester compound may have 4 to 10 carbon atoms.

That is, $R_2$ in Chemical Formula 1 may have 4 to 10 carbon atoms, preferably, 4 to 9 carbon atoms. Further, $R_2$ in Chemical Formula 1 may be a butyl group (B), an isobutyl group (iB), a pentyl group (P), a hexyl group (Hx), a heptyl group (Hp), an isoheptyl group (iHp), an octyl group (nO), a 2-ethylhexyl group (EH or O), a nonyl group (nN), an isononyl group (IN), a 6-methyloctyl group (MO), a decyl group (D), an isodecyl group (ID) or a 2-propylheptyl group (PH).

When $R_2$ in Chemical Formula 1 has 4 to 10 carbon atoms, excellent transparency (haze value) and volatile loss may be exhibited. Transparency is an important property in a plasticizer applied to a resin for a food wrapping material. Therefore, when transparency is poor, a plasticizer has no commerciality and thus cannot be applied, and when volatile loss is poor, a plasticizer is easily volatilized when heat is applied during processing and thus processability and workability become poor, thereby it may be difficult to apply a plasticizer to a resin for a food wrapping material. Accordingly, it may be preferable to adjust $R_2$ in the epoxidized alkyl ester compounds represented by Chemical Formula 1 to have 4 to 10 carbon atoms.

The epoxidized alkyl ester composition may have less than 4 carbon atoms, for example, 1 carbon atom. When a composition having a few number of carbon atoms such as epoxidized methyl ester or the like is applied, migration ability and volatile loss may be significantly poor, and transparency, adhesiveness and an elongation rate may be degraded. When an epoxidized alkyl ester having more than 10 carbon atoms is applied, the molecular weight is too high, and thus there is a concern that migration ability according to plasticization efficiency and compatibility with a resin may become a problem.

Therefore, an epoxidized alkyl ester included in the epoxidized alkyl ester composition may preferably have 4 to 10 carbon atoms, more preferably, 4, 8 or 9 carbon atoms.

In addition, the epoxidized alkyl ester composition represented by Chemical Formula 1 includes two or more compounds, and may be a composition formed by mixing two or more compounds having a different number of carbon atoms in $R_2$.

When two or more compounds are included, a composition may preferably formed by mixing a compound having 4 carbon atoms in $R_2$ and a compound having 8 carbon atoms in $R_2$ or by mixing a compound having 5 carbon atoms in $R_2$ and a compound having 9 carbon atoms in $R_2$.

The epoxidized alkyl ester composition may have an oxirane content (O.C.) of 3.5% or more, 4.0% or more, 4.2% or more, and preferably, 4.5% or more. Also, the epoxidized alkyl ester composition may have an iodine value of less than 3.5 g $I_2$/100 g (hereinafter, the unit "g $I_2$/100 g" is omitted), preferably, 3.2 or less, and more preferably, 3.0 or less.

When the epoxidized alkyl ester composition is applied to a plasticizer composition, the measured iodine value and oxirane content may be important factors. Particularly, in the case of a plasticizer composition included in a food wrapping material in which an environmentally-friendly property is essential, an iodine value and an oxirane content may affect properties of the plasticizer.

When an iodine value is 3.5 or more, properties may be below a level in the functional evaluation. For example, the color of a plasticizer composition may become dark, which may cause a problem in which a plasticizer composition is inappropriate for being used as a food wrapping material. Also, when an iodine value is less than 3.5, mechanical properties such as tensile strength and an elongation rate may be improved.

Therefore, the epoxidized alkyl ester composition may preferably have an iodine value of less than 3.5, more preferably, 3.2 or less, and most preferably, 3.0 or less. The iodine value refers to a content of double bonds present in a molecule, and may be derived from a value measured by titration through iodination of the double bond.

In addition, the oxirane content may vary depending on the number of epoxy groups contained in a substituent represented by $R_1$ in Chemical Formula 1, and may be 3.5% or more, 4.0% or more, 4.2% or more, and preferably, 4.5% or more. The oxirane content may be measured by titration, and may be measured by titration using a sample and acidic solution.

The iodine value refers to a content of double bonds, and the content of double bonds may be a content of double bonds which remain after epoxidation such as epoxidation of a vegetable oil or fatty acid alkyl ester. That is, the oxirane content and iodine value may be indicators to show an epoxidized degree, so they may be partially related to each other, and, theoretically, may be inversely proportional to each other.

However, since double bonds of a vegetable oil or fatty acid alkyl ester may be varied substantially depending on a material, the two parameters do not necessarily form an exact inverse or trade-off relationship, and a material having the higher iodine value may simultaneously have the higher oxirane content between two materials. Therefore, it may be preferable that an epoxidized alkyl ester compound having an iodine value and oxirane content in the above ranges be applied in a plasticizer composition used for an environmentally-friendly food wrapping material.

Meanwhile, the epoxidized alkyl ester compound may have an oxirane index (O.I.) of 1.0 or more.

The relationship between an iodine value and oxirane content is as described above, but simultaneously, it may be preferable that an oxirane index be 1.0 or more, optimally, 2.0 or more. The term "oxirane index" used herein refers to a ratio of an oxirane content of the epoxidized alkyl ester compound to an iodine value thereof, and may be a ratio of remaining double bonds that are not reacted and double bonds epoxidized through epoxidation.

Specifically, the oxirane index may be a ratio of an oxirane content to an iodine value, and may be, for example, 1.0 or more. That is, when a value obtained by dividing an oxirane content of the epoxidized alkyl ester by an iodine value thereof is 1.0 or more, it is possible to obtain a more optimized plasticizer composition.

The epoxidized alkyl ester composition may include an epoxy alkyl ester composition including one or more compounds represented by Chemical Formula 1, and may further include an alkyl ester composition including one or more compounds represented by the following Chemical Formula 2.

[Chemical Formula 2]

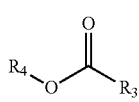

In Chemical Formula 2,
$R_3$ is an alkyl group having 8 to 20 carbon atoms, and $R_4$ is an alkyl group having 4 to 10 carbon atoms.

In the alkyl ester composition including one or more compounds represented by Chemical Formula 2, $R_3$ may not include an epoxy group. In a process of preparing an epoxy-based alkyl ester composition using an epoxidized oil and alcohol, a fatty acid moiety of the epoxidized oil may be varied, there may be a fatty acid moiety that is not bound to an epoxy group, and a compound may result from such a fatty acid moiety.

When such a saturated alkyl ester is included in a plasticizer composition, a separate purification process is not necessary, and thus a cost of a product may be improved. Also, when an alkyl ester composition, which has a few number of carbon atoms, that is, 8 to 18 and does not include oxirane, is contained, plasticization efficiency and migration ability may be improved. However, when a content of such a saturated alkyl ester composition is about 80 wt % or more with respect to the total plasticizer composition including an unsaturated epoxidized alkyl ester composition, compatibility with a vinyl chloride resin may be degraded. For this reason, when a composition ratio is 70 wt % or less, preferably, 50 wt % or less, and more preferably, 30 wt % or less, excellent compatibility with a vinyl chloride resin may be exhibited.

Method of Preparing Plasticizer Composition
Preparation of Epoxidized Alkyl Ester Composition In the present invention, a method of preparing a plasticizer composition may be performed by esterification.

According to an embodiment of the present invention, there is provided a method of preparing a plasticizer composition, which includes preparing an epoxidized alkyl ester composition by reacting an epoxidized oil with an alkyl alcohol having 4 to 10 carbon atoms, wherein the epoxidized alkyl ester composition has an iodine value of less than 3.5 g $I_2$/100 g.

Basic characteristics of the epoxidized alkyl ester compound such as an iodine value, an oxirane content and the like have been described above, and therefore will be omitted.

The reaction of an epoxidized oil and alkyl alcohol having 4 to 10 carbon atoms may be trans-esterification.

The term "trans-esterification" used herein refers to a reaction between an alcohol and an ester as shown in Reaction Scheme 1, in which R" of the ester and R' of the alcohol are interchanged:

[Reaction Formula 1]

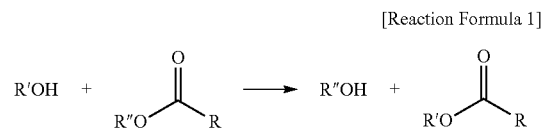

The trans-esterification may produce three types of ester compositions according to three cases in which an alkoxide of the alcohol attacks carbons of two ester (RCOOR") groups present in an ester-based compound; an alkoxide of the alcohol attacks carbons of one ester (RCOOR") group present in an ester-based compound; and there is no reaction between an alcohol and an ester group in an ester-based compound.

In addition, compared to acid-alcohol esterification, the trans-esterification does not cause water contamination, and may solve problems caused by the use of an acidic catalyst due to being performed without a catalyst.

According to the present invention, in the trans-esterification, the ester may be an epoxidized oil, and the alcohol may be a primary alcohol including an alkyl group having 4 to 10 carbon atoms. The alcohol may have 4 to 10 carbon atoms, preferably, 4 to 9 carbon atoms, and the alkyl group included in the alcohol may correspond to $R_2$ in Chemical Formula 1 after the reaction is completed.

Additionally, the epoxidized oil may be, for example, epoxidized soybean oil, epoxidized castor oil, epoxidized linseed oil, epoxidized palm oil, epoxidized stearate, epoxidized oleate, epoxidized tall oil, epoxidized linoleate, or a mixture thereof, and may be a compound prepared by introducing a predetermined amount of epoxy groups through epoxidation of a vegetable oil.

The epoxidized oil may be represented, for example, by the following Chemical Formula 3, may be a triglyceride-based compound including three ester groups in one molecule, and may contain a predetermined amount of epoxy groups.

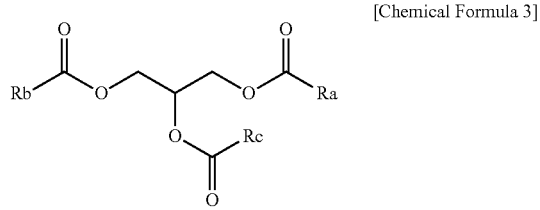

[Chemical Formula 3]

In Chemical Formula 3, Ra, Rb and Rc are each independently an alkyl group having 8 to 20 carbon atoms or an alkyl group having 8 to 20 carbon atoms and containing one or more epoxy groups. One or more of Ra, Rb and Rc are alkyl groups having 8 to 20 carbon atoms and containing one or more epoxy groups.

More specifically, the epoxidized oil may be, for example, a compound represented by the following Chemical Formula 3a.

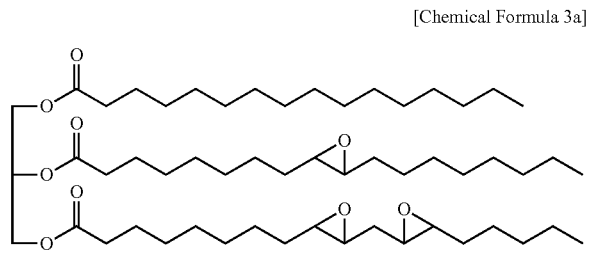 [SMILES: CCCCCCCCCCCCCCCC(=O)OCCC(CCOC(=O)CCCCCCCC1OC1CC1OC1CCCCC)OC(=O)CCCCCCCC1OC1CCCCCCCC]

[Chemical Formula 3a]

The epoxidized oil represented by Chemical Formula 3a is one example.

In addition, the epoxidized oil may have an iodine value of less than 3.5 (g $I_2$/100 g). The iodine value slightly fluctuates during trans-esterification and is not significantly different from an iodine value of an epoxidized alkyl ester compound as a product, which may be approximately equal to or slightly less than the iodine value of the epoxidized alkyl ester composition as described above.

Although the present invention is not limited thereto, when the epoxidized oil is selected and applied, the improvement of the color and solid content of a product may be controlled to more preferable level. Preferably, an oxirane content may be 6.0% or more (about 16.2% or more when converted into an epoxy content), and an iodine value may be 3.0 or less. When an epoxidized oil having the above oxirane content and iodine value is selected to prepare an epoxidized alkyl ester composition, the color and solid content of a product may be effectively improved.

When the epoxidized oil and alkyl alcohol having 4 to 10 carbon atoms are trans-esterified, all of the three ester groups may be separated. Accordingly, three or more types of epoxy-based ester compounds in which an alkyl group of the alcohol is newly bound may be formed.

Specifically, the epoxidized oil represented by Chemical Formula 3 and one or more alcohols represented by the following Chemical Formula 4 may be put into a reaction vessel, and trans-esterified to prepare an epoxidized alkyl ester composition.

Rd-OH                                    [Chemical Formula 4]

In Chemical Formula 4, Rd is an alkyl group having 4 to 10 carbon atoms.

The trans-esterification may be performed at 40 to 230° C., preferably, 50 to 200° C., and more preferably, 100 to 180° C. In an exemplary embodiment, the trans-esterification may be performed at 100 to 180° C. to control the production rate of solid in a final product.

In addition, the trans-esterification may be performed preferably for 30 minutes to 8 hours, more preferably, for 1 to 6 hours. Also, in consideration of quality of a final product, the reaction is preferably performed for at least 3 hours, and it is more preferable that a reaction time of at least 4 hours is secured. Although the reaction is preferably performed up to 6 hours, when the reaction is performed for at least 4 hours, the viscosity and solid content of a product may be improved to an intended level. However, when a reaction time is above 8 hours, an oxirane content is affected, an oxirane content is decreased, and thus the quality of a product such as color and the like may be adversely affected.

Within the above temperature and time ranges, a desired epoxidized alkyl ester composition may be effectively obtained. Here, the reaction time may be calculated from the point of time to reach the reaction temperature after temperature rising for the reactants.

The trans-esterification may be performed under a basic, acidic or metal catalyst, which provides an effect of reducing the reaction time.

The acidic catalyst may be, for example, sulfuric acid, methanesulfonic acid or p-toluenesulfonic acid, and the metal catalyst may be, for example, an alkoxide-based organic metal catalyst containing sodium or potassium, a metal oxide catalyst, a metal salt catalyst or a metal itself.

The metal component may be, for example, any one or a mixture of two or more selected from the group consisting of sodium, potassium, tin, titanium and zirconium.

Purification of Epoxidized Alkyl Ester Composition

In addition, a process of removing a polyhydric alcohol and a reaction by-product produced after the trans-esterification and an unreacted alcohol through separation, washing and distillation may be further performed.

In the purification, specifically, cooling and keeping the reaction by-products at 80 to 100° C. for a predetermined time after the trans-esterification may be performed. In this case, layer separation occurs, in which an upper layer may include an epoxidized alkyl ester and alcohol and a lower layer may include glycerine and other by-products. Next, in order to neutralize a catalyst, an aqueous solution for neutralizing a catalyst may be added to induce neutralization and washing.

The neutralization and washing processes may be performed after a lower layer mainly including by-products is first separated. In the neutralization and washing processes, by-products included in a lower layer may be dissolved in water and discharged. Afterward, washing may be repeatedly performed to recover and remove an unreacted alcohol and moisture.

However, it may be necessary to vary the neutralization and washing processes according to the number of carbon atoms of an alcohol used in the trans-esterification.

For example, in the case of using butanol having 4 carbon atoms, when the neutralization and washing processes are directly performed, waste water may be produced, and therefore, it may be preferable to pre-remove butanol through distillation. However, in this case, since activity of a catalyst remains, glycerol as a by-product and an epoxidized alkyl ester as a product may be reversely reacted to produce an epoxidized oil-like material such as a diglyceride, a triglyceride or the like. Therefore, it is necessary to pay attention to the design of a process.

As another example, when 2-ethylhexyl alcohol having 8 carbon atoms is used, wastewater is not produced due to low solubility of 2-ethylhexyl alcohol in water. Therefore, both cases in which an alcohol is removed after neutralization and washing processes and in which neutralization and washing processes are performed after by-products in a lower layer are removed may be progressed without critical problems.

Resin Composition

The plasticizer composition thus prepared may be included at 5 to 150 parts by weight, 10 to 100 parts by weight, or 30 to 60 parts by weight with respect to 100 parts by weight of a resin such as ethylene vinyl acetate, polyethylene, polyketone, polypropylene, polyvinyl chloride, polystyrene, polyurethane, a thermoplastic elastomer or a mixture thereof, and may be included at 70 to 130 parts by weight according to the use.

The resin composition may be processed by various methods such as plastisol, extrusion, injection and calendaring processes, and may be applied to electric wires, interior materials for automobiles, films, sheets, tubes, wallpaper, toys, flooring materials, wires or covering materials of optical fibers.

In addition, the resin composition may be designed to be used in the medical or food industry. For example, the resin composition may be applied to a blood bag, intravenous bag, saline bag, syringe, intravenous tube, nasogastric tube, catheter, drainage tube, medical glove, oxygen mask, retainer, artificial skin and food wrapping material (e.g., various wrapping materials for beverages, meat and frozen vegetables).

Preferably, the resin composition may be applied to a resin for an environmentally-friendly food wrapping material or a medical resin, and may obtain an excellent evaluation in the evaluation of functionality such as transparency and color so as to be suitable for the above application, may exhibit excellent adhesiveness, and may also exhibit basic mechanical properties such as tensile strength, an elongation rate, plasticization efficiency and volatile loss equal to or higher than those of an existing plasticizer.

In the resin composition, a stabilizer, an anti-fog agent or the like may be further added and other additives may also be further added.

EXAMPLE

Hereinafter, embodiments will be described in detail for promoting an understanding of the present invention. However, embodiments of the present invention may be modified in several different forms, and the scope of the present invention is not limited to the embodiments to be described below. The embodiments of the present invention are provided so that this disclosure will be thorough and complete, and will fully convey the concept of embodiments to those skilled in the art.

BEST MODE

Example 1

1,000 g of epoxidized soybean oil (ESO) having an oxirane content of 6.97% and an iodine value of 1.93 (g $I_2$/100 g), 500 g of 2-ethylhexyl alcohol (2-EH) and 5.5 g of a metallic salt catalyst as a catalyst were input to a 3 L 4-neck reaction vessel equipped with a cooler, a condenser, a decanter, a reflux pump, a temperature controller, an stirrer and the like, and a temperature was slowly increased to about 180° C.

After it was confirmed through gas chromatography that ESO as a raw material was completely reacted and thus consumed, the reaction was terminated. After the reaction was completed, glycerine as a by-product and an unreacted raw material were removed, and a product was purified to finally obtain 1,210 g of an epoxidized 2-ethylhexyl ester composition having an oxirane content of 5.21% and an iodine value of 1.70 g $I_2$/100 g.

Example 2

An epoxidized butyl ester composition was prepared in the same manner as in Example 1 except that butanol was used instead of 2-ethylhexanol, and used as a plasticizer. In this case, the oxirane content and iodine value of an epoxidized oil and the prepared epoxidized alkyl ester composition were measured, results of which are shown in the following Table 1.

Example 3

An epoxidized isononyl ester composition was prepared in the same manner as in Example 1 except that isononanol was used instead of 2-ethylhexanol, and used as a plasticizer. In this case, the oxirane content and iodine value of an epoxidized oil and the prepared epoxidized alkyl ester composition were measured, results of which are shown in the following Table 1.

Example 4

An epoxidized butyl ester and epoxidized 2-ethylhexyl ester composition was prepared in the same manner as in Example 1 except that butanol and 2-ethylhexanol were used in a weight ratio of 5:5 instead of 2-ethylhexanol, and used as a plasticizer. In this case, the oxirane content and iodine value of an epoxidized oil and the prepared epoxidized alkyl ester composition were measured, results of which are shown in the following Table 1.

Example 5

An epoxidized pentyl ester and epoxidized isononyl ester composition was prepared in the same manner as in Example 1 except that pentanol and isononanol were used in a weight ratio of 5:5 instead of 2-ethylhexanol, and used as a plasticizer. In this case, the oxirane content and iodine value of an epoxidized oil and the prepared epoxidized alkyl ester composition were measured, results of which are shown in the following Table 1.

Example 6

An epoxidized 2-ethylhexyl ester composition was prepared in the same manner as in Example 1 except that ESO having an oxirane content of 4.73% and an iodine value of 3.80 (g $I_2$/100 g) was used, and used as a plasticizer. In this case, the oxirane content and iodine value of an epoxidized oil and the prepared epoxidized alkyl ester composition were measured, results of which are shown in the following Table 1.

Example 7

An epoxidized 2-ethylhexyl ester composition was prepared in the same manner as in Example 1 except that ESO having an oxirane content of 4.98% and an iodine value of 2.32 (g $I_2$/100 g) was used, and used as a plasticizer. In this case, the oxirane content and iodine value of an epoxidized oil and the prepared epoxidized alkyl ester composition were measured, results of which are shown in the following Table 1.

Comparative Example 1

An epoxidized methyl ester composition was prepared in the same manner as in Example 1 except that methanol was used instead of 2-ethylhexanol, and used as a plasticizer. In this case, the oxirane content and iodine value of an epoxidized oil and the prepared epoxidized alkyl ester composition were measured, results of which are shown in the following Table 1.

Comparative Example 2

An epoxidized propyl ester composition was prepared in the same manner as in Example 1 except that propanol was used instead of 2-ethylhexanol, and used as a plasticizer. In this case, the oxirane content and iodine value of an epoxidized oil and the prepared epoxidized alkyl ester composition were measured, results of which are shown in the following Table 1.

Comparative Example 3

An epoxidized dodecyl ester (epoxidized fatty acid dodecyl ester (eFADDE)) composition was prepared in the same manner as in Example 1 except that dodecanol was used instead of 2-ethylhexanol, and used as a plasticizer. In this case, the oxirane content and iodine value of an epoxidized oil and the prepared epoxidized alkyl ester composition were measured, results of which are shown in the following Table 1.

Comparative Example 4

An epoxidized 2-ethylhexyl ester composition was prepared in the same manner as in Example 1 except that ESO having an oxirane content of 4.70% and an iodine value of 4.02 (g $I_2$/100 g) was used, and used as a plasticizer. In this case, the oxirane content and iodine value of an epoxidized oil and the prepared epoxidized alkyl ester composition were measured, results of which are shown in the following Table 1.

Comparative Example 5

An epoxidized 2-ethylhexyl ester composition was prepared in the same manner as in Example 1 except that ESO having an oxirane content of 2.07% and an iodine value of 8.90 (g $I_2$/100 g) was used, and used as a plasticizer. In this case, the oxirane content and iodine value of an epoxidized oil and the prepared epoxidized alkyl ester composition were measured, results of which are shown in the following Table 1.

Comparative Example 6 (Comparative Example for Treatment of Wrap Film)

EBN.WG (LG Chem), a commercially available plasticizer for a wrap film, was applied as a plasticizer.

Measurement of Iodine Value and Oxirane Content

For each of the compositions prepared in examples and comparative examples, the oxirane content and iodine value of an epoxidized oil and the epoxidized alkyl ester composition were measured, results of which are shown in the following Table 1. In this case, the oxirane content was measured with reference to ASTM D1652, and the iodine value was measured with reference to ASTM D5768.

TABLE 1

| | | Epoxidized oil | | Epoxidized alkyl ester | |
|---|---|---|---|---|---|
| | Plasticizer | Iodine value | Oxirane content (%) | Iodine value | Oxirane content (%) |
| Example 1 | eFAEHE | 1.93 | 6.97 | 1.70 | 5.21 |
| Example 2 | eFABE | 1.93 | 6.97 | 1.68 | 5.18 |
| Example 3 | eFAINE | 1.93 | 6.97 | 1.71 | 5.22 |
| Example 4 | eFABE + eFAEHE | 1.93 | 6.97 | 1.72 | 5.26 |
| Example 5 | eFAPE + eFAINE | 1.93 | 6.97 | 1.68 | 5.24 |
| Example 6 | eFAEHE | 3.80 | 4.73 | 3.46 | 3.58 |
| Example 7 | eFAEHE | 2.32 | 4.98 | 1.98 | 3.61 |
| Comparative Example 1 | eFAME | 1.93 | 6.97 | 1.80 | 5.13 |
| Comparative Example 2 | eFAPE | 1.93 | 6.97 | 1.82 | 5.20 |
| Comparative Example 3 | eFADDE | 1.93 | 6.97 | 1.78 | 5.33 |
| Comparative Example 4 | eFAEHE | 4.02 | 4.70 | 3.95 | 3.50 |
| Comparative Example 5 | eFAEHE | 8.90 | 2.07 | 7.71 | 1.55 |

Experimental Example 1: Evaluation of Epoxidized Alkyl Ester Composition (Compatibility with Resin and Discoloration)

Experiments were conducted to identify effects of the iodine values and oxirane contents in examples and comparative examples shown in Table 1 on compatibility with polyvinyl chloride (PVC) and the discoloration degree of a liquid product.

Compatibility with Resin

Each of products according to examples and comparative examples was used as a plasticizer composition. Specifically, 60 parts by weight of each of the plasticizer compositions was mixed with 100 parts by weight of PVC (LS100S) using a 3 L super mixer at 98° C. and 700 rpm, and then a migration (or bleeding) degree of the plasticizer in the resin was observed while the resulting mixture was stored in a convection oven at 80° C. for a long time. In this case, the migration degree, which was expressed as a value of 0 to 5 (compatibility is excellent as the value is close to 0 and compatibility is poor as the value is close to 5), is shown in the following Table 2.

TABLE 2

| | | Epoxidized alkyl ester | | Compatibility with resin (80° C.) | |
|---|---|---|---|---|---|
| | Plasticizer | Iodine value | Oxirane content (%) | 1 week | 2 weeks |
| Example 1 | eFAEHE | 1.70 | 5.21 | 0 | 1 |
| Example 2 | eFABE | 1.68 | 5.18 | 0 | 0 |
| Example 3 | eFAINE | 1.71 | 5.22 | 0 | 1 |
| Example 6 | eFAEHE | 3.46 | 3.58 | 0.5 | 2 |
| Comparative Example 4 | eFAEHE | 3.95 | 3.50 | 1.0 | 3 |
| Comparative Example 5 | eFAEHE | 7.71 | 1.55 | 2 | 5 |

Referring to Table 2, it can be seen that compatibilities with a resin were significantly different according to the iodine value and oxirane content. That is, it can be seen that the plasticizer compositions according to Comparative Examples 4 and 5 having significantly high iodine values had considerably poor compatibility with a resin when just stored for about 2 weeks. Therefore, it can be seen that it is necessary to appropriately adjust the iodine value and oxirane content of an epoxidized alkyl ester composition.

In addition, it was confirmed that, when an iodine value was increased by about 100% from 1.71 in Example 3 to 3.46 in Example 6, compatibility was increased by 0.5, but even when an iodine value was increased just by about 14% from 3.46 in Example 6 to 3.95 in Comparative Example 4, compatibility was also increased by 0.5. Therefore, it can be seen that it is necessary to appropriately adjust the iodine value.

Liquid Discoloration

A predetermined amount of each of liquid products according to examples and comparative examples was put into a 100 ml glass vessel, and then a discoloration degree of a liquid plasticizer product was observed while the liquid products were stored in a convection oven at 80° C. for a long time. The discoloration degree was measured with a colormeter, results of which are shown in the following Table 3.

TABLE 3

| | | Epoxidized alkyl ester | | Discoloration of product (80° C.) | |
|---|---|---|---|---|---|
| | Plasticizer | Iodine value | Oxirane content (%) | Initial stage (APHA) | 2 weeks (APHA) |
| Example 1 | eFAEHE | 1.70 | 5.21 | 95 | 110 |
| Example 2 | eFABE | 1.68 | 5.18 | 100 | 115 |
| Example 3 | eFAINE | 1.71 | 5.22 | 90 | 105 |
| Example 6 | eFAEHE | 3.46 | 3.58 | 155 | 230 |
| Comparative Example 4 | eFAEHE | 3.95 | 3.50 | 160 | 310 |
| Comparative Example 5 | eFAEHE | 7.71 | 1.55 | 180 | 365 |

Referring to Table 3, it was confirmed that the discoloration degree of a product was significantly different according to the iodine value and oxirane content. That is, it can be seen that the plasticizer composition according to Comparative Example 5 having a significantly high iodine value exhibited a significantly poor discoloration degree when just stored for about 2 weeks. Therefore, it can be seen that it is necessary to appropriately adjust the iodine value and oxirane content of an epoxidized alkyl ester composition to obtain a product having excellent chromaticity.

Experimental Example 2: Evaluation of Properties 1 (Treatment of Sheet)

Each specimen was prepared, according to ASTM D638, by mixing 30 parts by weight of each of the plasticizer compositions according to Examples 1 to 7 and Comparative Examples 1 to 5 and 3 parts by weight of a stabilizer (BZ-153T) with 100 parts by weight of PVC (LS100S) using a 3 L super mixer at 98° C. and 700 rpm, roll milling the resulting mixture at 160° C. for 4 minutes to prepare a 5-mm sheet, and performing pressing at 180° C. under low pressure for 2.5 minutes, and under high pressure for 2 minutes to prepare 1T and 3T sheets. Properties of each specimen were evaluated by test items listed below, results of which are shown in the following Table 4.

<Test Items>

Evaluation was conducted by test items listed below for examples and comparative examples.

Measurement of Hardness

According to ASTM D2240, Shore (Shore D) hardness was measured at 25° C. under 3T and 10 s conditions.

Measurement of Tensile Strength

According to ASTM D638, each specimen was pulled at a cross head speed of 200 mm/min (1T) using a tester, U.T.M (Manufacturer; Instron, Model No.; 4466), and then a position at which the specimen was broken was detected. A tensile strength was calculated as follows:

Tensile strength (kgf/mm$^2$)=Load value (kgf)/Thickness (mm)×Width (mm)

Measurement of Elongation Rate

According to ASTM D638, each specimen was pulled at a cross head speed of 200 mm/min (1T) using the tester, U.T.M, and then a position at which the specimen was broken was detected. An elongation rate was calculated as follows:

Elongation rate (%)=Length after elongation/Initial length×100

Measurement of Migration Loss

A test specimen having a thickness of 2 mm or more was prepared according to KSM-3156, PS plates were attached to both sides of the specimen, and then a load of 1 kgf/cm$^2$ was applied to the specimen. The specimen was kept in a convection oven (80° C.) for 72 hours, and cooled at room temperature for 4 hours. Then, after the PS attached to both sides of the specimen was removed, weights before and after the specimen was kept in the oven were measured. A migration loss was calculated by the equation as follows:

Migration loss (%)={(Initial weight of specimen at room temperature−Weight of specimen after being kept in oven)/Initial weight of specimen at room temperature}×100

Measurement of Volatile Loss

The prepared specimen was processed at 80° C. for 72 hours, and then a weight of the specimen was measured as follows:

Volatile loss (wt %)=Initial weight of specimen−(Weight of specimen after processed at 80° C. for 72 hours)/Initial weight of specimen×100

TABLE 4

| | Hardness (Shore D) | Tensile strength (kg/cm²) | Elongation rate (%) | Migration loss (%) | Volatile loss (%) |
|---|---|---|---|---|---|
| Example 1 | 54.8 | 245.4 | 288.5 | 2.19 | 0.74 |
| Example 2 | 52.5 | 243.1 | 280.6 | 1.56 | 1.20 |
| Example 3 | 55.7 | 250.3 | 290.5 | 2.30 | 0.55 |
| Example 4 | 53.4 | 246.5 | 285.7 | 0.98 | 1.02 |
| Example 5 | 54.3 | 247.6 | 286.0 | 1.90 | 0.88 |
| Example 6 | 55.0 | 234.0 | 271.3 | 2.74 | 1.25 |
| Example 7 | 54.9 | 235.7 | 273.5 | 2.65 | 1.15 |
| Comparative Example 1 | 52.1 | 221.0 | 250.3 | 6.71 | 11.58 |
| Comparative Example 2 | 53.0 | 230.8 | 258.9 | 5.04 | 8.52 |
| Comparative Example 3 | 58.4 | 260.4 | 275.1 | 3.56 | 0.51 |
| Comparative Example 4 | 55.3 | 203.4 | 270.6 | 2.80 | 1.33 |
| Comparative Example 5 | 60.2 | 245.0 | 232.1 | 10.5 | 9.57 |

Referring to Table 4, it was confirmed that the plasticizer compositions according to Examples 1 to 7 were excellent in all properties in balance without any one poor property, whereas the plasticizer compositions according to Comparative Examples 1 to 5 were poor in all properties or particularly poor in any one or two or more properties. Therefore, it can be seen that it is difficult to apply the plasticizer compositions according to Comparative Examples 1 to 5 as plasticizer compositions.

Specifically, it can be seen that, in the case of Comparative Examples 1 and 2, a considerable amount of components was volatilized during a process because the epoxidized alkyl ester compositions had a few number of carbon atoms, that is, 1 and 3, and properties were significantly degraded according thereto, resulting in high migration loss and volatile loss. However, it was confirmed that, in the case of Example 2 in which an epoxidized alkyl ester composition had 4 carbon atoms, hardness (plasticization efficiency) was maintained at a level similar to that in Comparative Examples 1 and 2, but volatile loss and migration loss were significantly low although a difference in the number of carbon atoms is not relatively large, resulting in significantly improved properties.

In addition, it was confirmed that, in the case of Comparative Example 3, high migration loss was exhibited compared to examples because the number of carbon atoms was 12, which is too large, resulting in poor properties. Also, it was confirmed that significantly high hardness (plasticization efficiency) was exhibited compared to Examples 1 and 3 in which each of the number of carbon atoms was 8 and 9, resulting in poor plasticization efficiency.

Additionally, it was confirmed that tensile strength was sharply degraded in the case of Comparative Example 4 in which an iodine value was 3.5 or more, and poor compatibility with a resin was exhibited in the case of Comparative Example 5 in which both an iodine value and an oxirane content were not satisfactory, thereby processing itself is difficult, the mixing with the resin cannot be smoothly performed, and all properties of the resin specimen such as hardness, an elongation rate, migration loss, volatile loss were poor.

Experimental Example 3: Evaluation of Properties 2 (Treatment of Wrap Film)

The plasticizers according to Examples 1 to 3 and Comparative Examples 1 to 3 and 6 were used as test specimens. Each specimen was prepared, according to ASTM D638, by mixing 40.5 parts by weight of each of the plasticizers, 7.2 parts by weight of ESO as an auxiliary stabilizer, 2.16 parts by weight of an anti-fog agent (Almax-9280) and 1.17 parts by weight of a stabilizer (LTX-630P) with 100 parts by weight of PVC in a 3 L super mixer at 98° C. and 700 rpm, roll milling the resulting mixture at 160° C. for 4 minutes, and performing pressing at 180° C. for 2.5 minutes (low pressure) and for 2 minutes (high pressure) to manufacture a wrap film. Properties of each specimen were evaluated by test items listed below, results of which are shown in the following Table 5.

<Additional Test Items>
Measurement of Hardness
According to ASTM D2240, Shore (Shore A) hardness was measured at 25° C. under 3T and 10s conditions.
100% Modulus
According to ASTM D638, each specimen was pulled at a cross head speed of 200 mm/min (1T) using the tester, U.T.M, and then a force when the specimen was subjected to 100% strain was measured.
Transparency
A haze value was measured with a haze meter. The haze value is an indicator to show a degree of turbidity of a film, and it was evaluated that as a value is low, transparency is excellent.
Evaluation of Adhesiveness
An adhesion degree was evaluated into 5 scales by touching the film by hand, and it was evaluated that 1 was excellent and 5 was poor.

TABLE 5

| | Hardness (Shore A) | Tensile strength (kg/cm²) | Elongation rate (%) | 100% modulus (%) | Migration loss (%) | Volatile loss (%) | Haze (%) | Adhesiveness |
|---|---|---|---|---|---|---|---|---|
| Example 1 | 69.5 | 189.7 | 337.9 | 74.7 | 2.08 | 0.73 | 3.95 | 2 |
| Example 2 | 67.5 | 196.3 | 317.7 | 85.9 | 1.06 | 2.39 | 3.21 | 1 |
| Example 3 | 71.0 | 186.0 | 312.5 | 86.9 | 2.03 | 0.57 | 4.67 | 2 |
| Comparative Example 1 | 65.4 | 165.4 | 284.1 | 88.7 | 4.50 | 8.30 | 3.55 | 5 |
| Comparative Example 2 | 66.8 | 168.9 | 290.5 | 90.1 | 4.20 | 6.58 | 3.87 | 3 |
| Comparative Example 3 | 73.6 | 190.5 | 308.7 | 108.6 | 2.11 | 0.50 | 5.67 | 5 |
| Comparative Example 6 | 70.2 | 192.6 | 309.7 | 95.1 | 2.45 | 2.59 | 4.31 | 2 |

Referring to Table 5, it can be seen that results were similar to the results in Experimental Example 2. That is, it can be seen that the epoxidized alkyl ester compositions according to Comparative Examples 1 and 2 in which each of the number of carbon atoms was 1 and 3, exhibited significantly poor migration loss and volatile loss, also exhibited poor adhesiveness, and thus are not appropriate to be used as wrapping materials. Also, it can also be seen that an elongation rate and tensile strength also were significantly low.

In addition, it can be seen that, in the case of Comparative Example 3, a high haze value was exhibited because the number of carbon atoms was 12, which is too large, and poor adhesiveness was also exhibited. Also, it can be seen that plasticization efficiency was degraded due to high hardness.

Further, it can be seen that when the plasticizers according to Examples 1 to 3 were applied, an elongation rate and 100% modulus may be improved compared to Comparative Example 6 in which a commercially available plasticizer was used. Also, it can be seen that the plasticizers applied to wrapping materials may be easily stretched and not broken.

The invention claimed is:

1. A plasticizer composition comprising an epoxidized alkyl ester composition including one or more compounds represented by the following Chemical Formula 1 and having an iodine value (I.V.) of less than 3.5 g $I_2$/100 g, as measured in accordance with ASTM D5768:

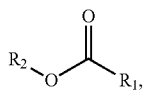

[Chemical Formula 1]

wherein $R_1$ is an alkyl group having 8 to 20 carbon atoms and including one or more epoxy groups and $R_2$ is an alkyl group having 4 to 10 carbon atoms; and an alkyl ester composition including one or more compounds represented by the following Chemical Formula 2:

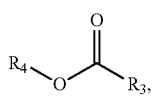

[Chemical Formula 2]

wherein $R_3$ is an alkyl group having 8 to 20 carbon atoms and $R_4$ is an alkyl group having 4 to 10 carbon atoms.

2. The plasticizer composition according to claim 1, wherein $R_2$ in Chemical Formula 1 is selected from the group consisting of a butyl group, an isobutyl group, a pentyl group, a hexyl group, a heptyl group, an isoheptyl group, an octyl group, a 2-ethylhexyl group, a nonyl group, an isononyl group, a 6-methyloctyl group, a decyl group, an isodecyl group and a 2-propylheptyl group.

3. The plasticizer composition according to claim 1, wherein $R_2$ in Chemical Formula 1 is selected from the group consisting of a butyl group, an isobutyl group, a 2-ethylhexyl group, an isononyl group, a 6-methyloctyl group and a 2-propylheptyl group.

4. The plasticizer composition according to claim 1, wherein the epoxidized alkyl ester composition comprises two or more compounds having a different number of carbon atoms in $R_2$ of Chemical Formula 1.

5. The plasticizer composition according to claim 1, wherein the epoxidized alkyl ester composition has an oxirane content (O.C.) of 3.5% or more, as measured in accordance with ASTM D1652.

6. The plasticizer composition according to claim 1, wherein the epoxidized alkyl ester composition has an oxirane index (O.I.) of 1.0 or more,
wherein O.I. is a ratio of an oxirane content of the epoxidized alkyl ester compound to an iodine value thereof, as measured in accordance with ASTM D1652 and ASTM D5768 respectively.

7. A resin composition comprising:
100 parts by weight of a resin; and
5 to 150 parts by weight of the plasticizer composition according to claim 1.

8. The resin composition according to claim 7, wherein the resin is one or more selected from the group consisting of ethylene vinyl acetate, polyethylene, polyketone, polypropylene, polyvinyl chloride, polystyrene, polyurethane and a thermoplastic elastomer.

9. The resin composition according to claim 7, wherein the resin composition is applied in preparation of one or more selected from the group consisting of electric wires, flooring materials, interior materials for automobiles, films, sheets, wallpaper and tubes.

10. The resin composition according to claim 7, wherein the resin composition is applied in preparation of one or more selected from the group consisting of a blood bag, intravenous bag, saline bag, syringe, intravenous tube, nasogastric tube, catheter, drainage tube, medical glove, oxygen mask, retainer, artificial skin and food wrapping material.

* * * * *